US006274591B1

(12) United States Patent
Foss et al.

(10) Patent No.: US 6,274,591 B1
(45) Date of Patent: *Aug. 14, 2001

(54) USE OF METHYLNALTREXONE AND RELATED COMPOUNDS

(76) Inventors: Joseph F. Foss, 4338 N. Clarendon, Apt. 3, Chicago, IL (US) 60613; Michael F. Roizen, 5622 S. Woodlawn Ave.; Jonathan Moss, 5827 S. Blackstone, both of Chicago, IL (US) 60637; Chun-Su Yuan, 940 E. 55th St., Chicago, IL (US) 60615; William Drell, 4566 Sherlock Ct., San Diego, CA (US) 92122

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/120,703

(22) Filed: Jul. 22, 1998

Related U.S. Application Data

(63) Continuation-in-part of application No. 08/962,742, filed on Nov. 3, 1997, now Pat. No. 5,972,954.

(51) Int. Cl.⁷ .................................................. A61K 31/448
(52) U.S. Cl. ............................................................ 514/282
(58) Field of Search ............................................. 514/282

(56) References Cited

U.S. PATENT DOCUMENTS

| | | | |
|---|---|---|---|
| 4,176,186 | 11/1979 | Goldberg et al. | 424/260 |
| 4,311,833 | 1/1982 | Namikoshi et al. | 536/90 |
| 4,377,568 | 3/1983 | Chopra | 424/31 |
| 4,385,078 | 5/1983 | Onda et al. | 427/3 |
| 4,457,907 | 7/1984 | Porter | 424/7.1 |
| 4,462,839 | 7/1984 | McGinley et al. | 106/198 |
| 4,518,433 | 5/1985 | McGinley et al. | 106/180 |
| 4,556,552 | 12/1985 | Porter et al. | 424/32 |
| 4,606,909 | 8/1986 | Bechgaard et al. | 424/21 |
| 4,615,885 | 10/1986 | Nakagame et al. | 424/94 |
| 4,670,287 | 6/1987 | Tsuji | 427/3 |
| 4,987,136 | 1/1991 | Kreek et al. | 514/282 |
| 5,536,507 | 7/1996 | Abramowitz et al. | 424/479 |
| 5,567,423 | 10/1996 | Ying | 424/94.3 |
| 5,591,433 | 1/1997 | Michael et al. | 424/184.1 |
| 5,597,564 | 1/1997 | Ying | 424/94.65 |
| 5,609,871 | 3/1997 | Michael et al. | 424/184.1 |
| 5,614,222 | 3/1997 | Kaplan | 424/489 |
| 5,626,875 | 5/1997 | Rodes et al. | 424/464 |
| 5,629,001 | 5/1997 | Michael et al. | 424/234.1 |
| 5,811,451 | 9/1998 | Minoia et al. | 514/443 |
| 5,866,164 | 2/1999 | Kuczynski et al. | 424/472 |

FOREIGN PATENT DOCUMENTS

WO98/25613  6/1995  (WO).
WO97/33566  9/1997  (WO).

OTHER PUBLICATIONS

Yuan, Chun Su et al., *European Journal of Pharmacology*, 276:107–111, 1995.

Yuan, Chun Su et al., *Clinical Pharmacology & Therapeutics*, 61:467–75, 1997.

Foss, Joseph F., *The Journal of Clinical Pharmacology*, 1997;37:25–30.

Yuan, Chun Su et al., *Clinical Pharmacology & Therapeutics*, 59:469–75, 1996.

*Primary Examiner*—Phyllis G. Spivack
(74) *Attorney, Agent, or Firm*—Christie, Parker & Hale, LLP

(57) ABSTRACT

A method for preventing or treating the opioid induced side effect, inhibition of gastrointestinal motility is disclosed. The method comprises administering methylnaltrexone or another quaternary derivative of noroxymorphone to a patient prior to the administration of an opioid or after the onset of side effects induced by the administration of an opioid, wherein the methylnaltrexone or quaternary derivative is administered orally in an enterically coated form.

30 Claims, 4 Drawing Sheets

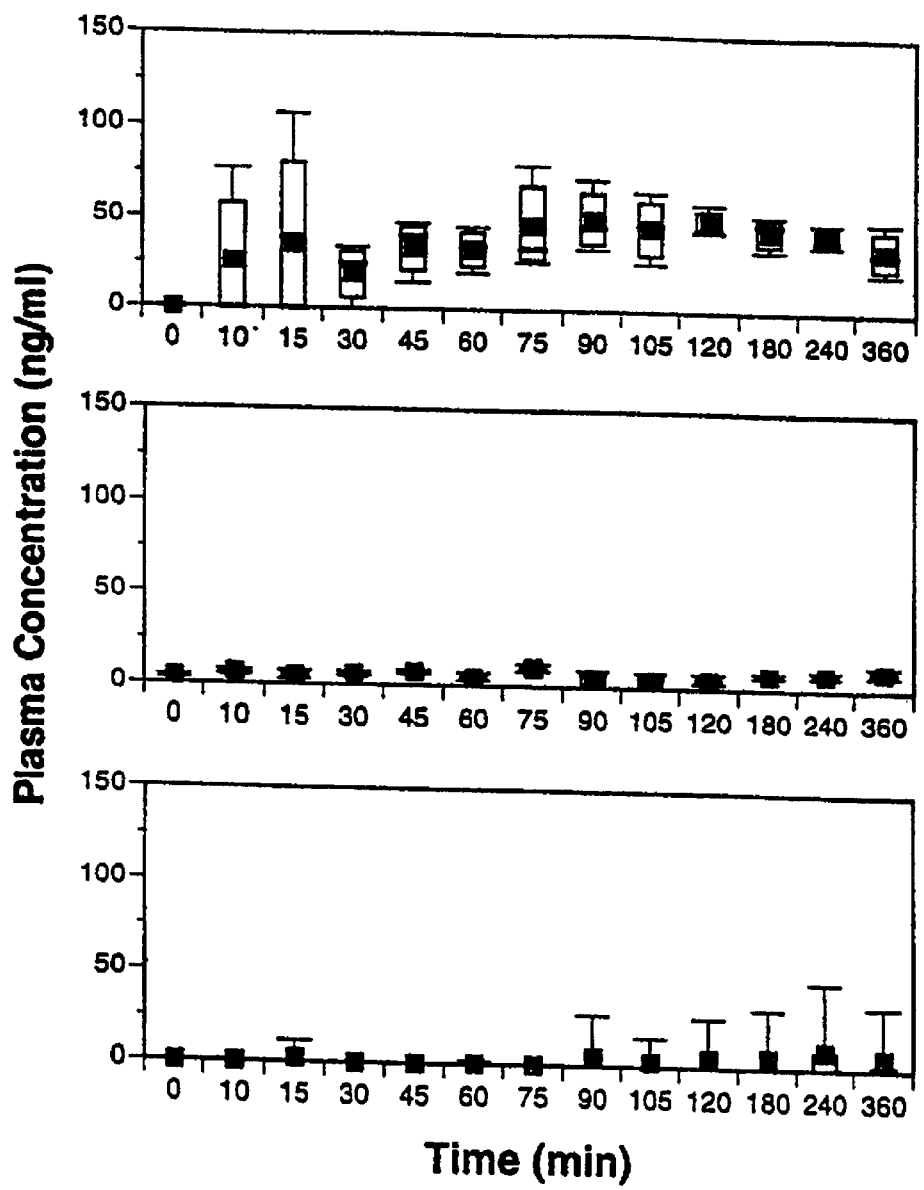
A. After regular MNTX 6.4 mg/kg, n=3
B. After enteric coated MNTX 6.4 mg/kg, n =3
C. After enteric coated MNTX 3.2 mg/kg, n =9

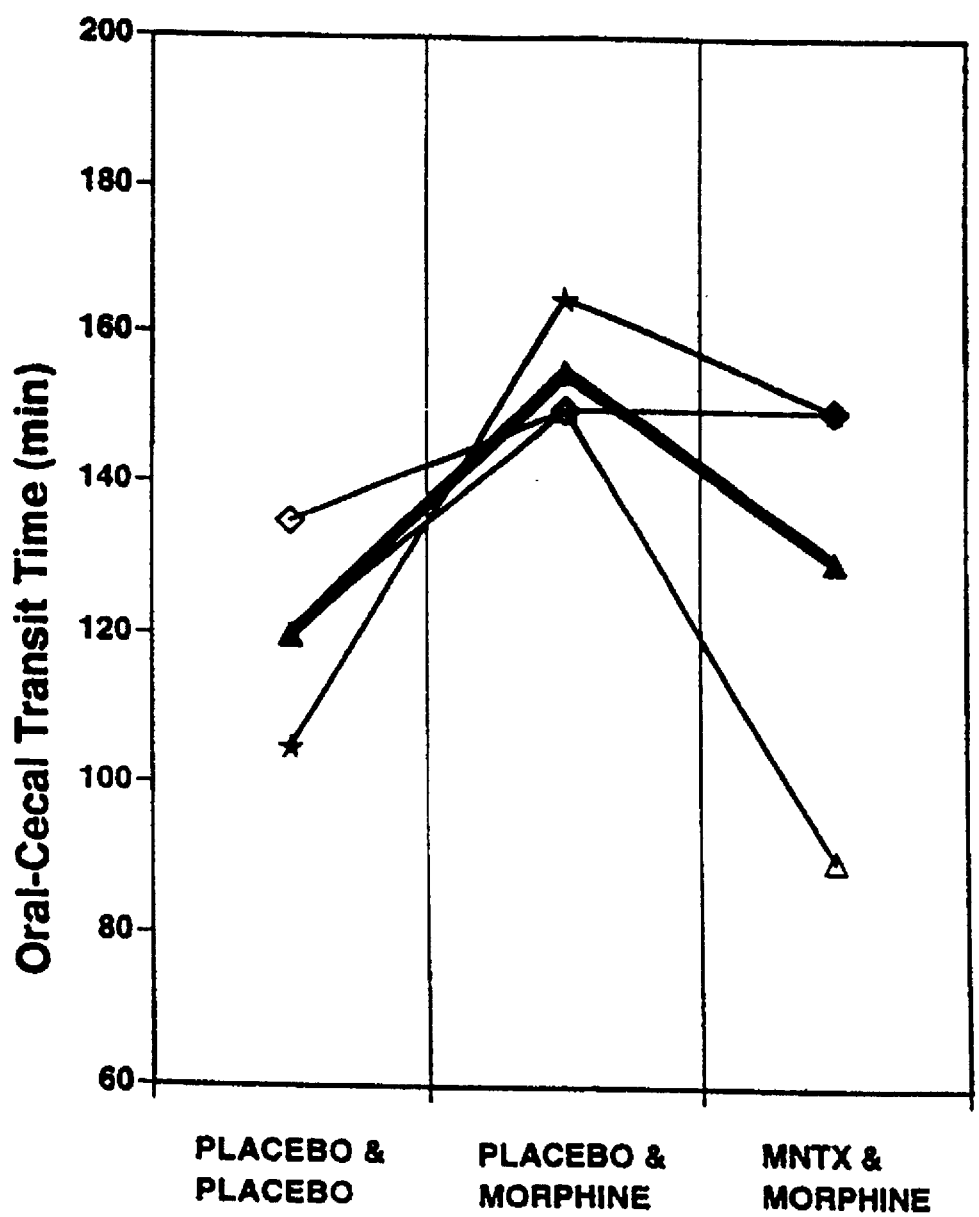

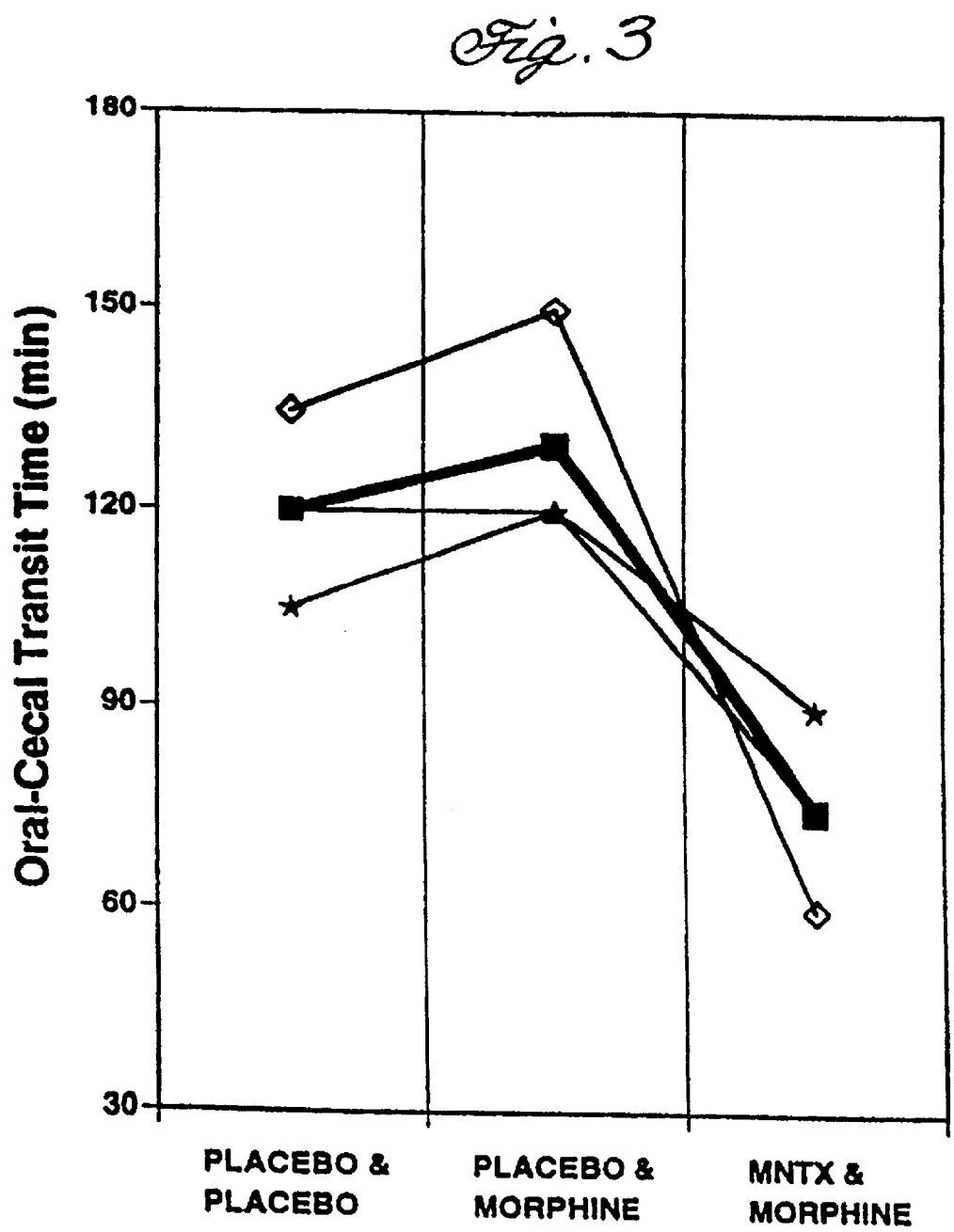

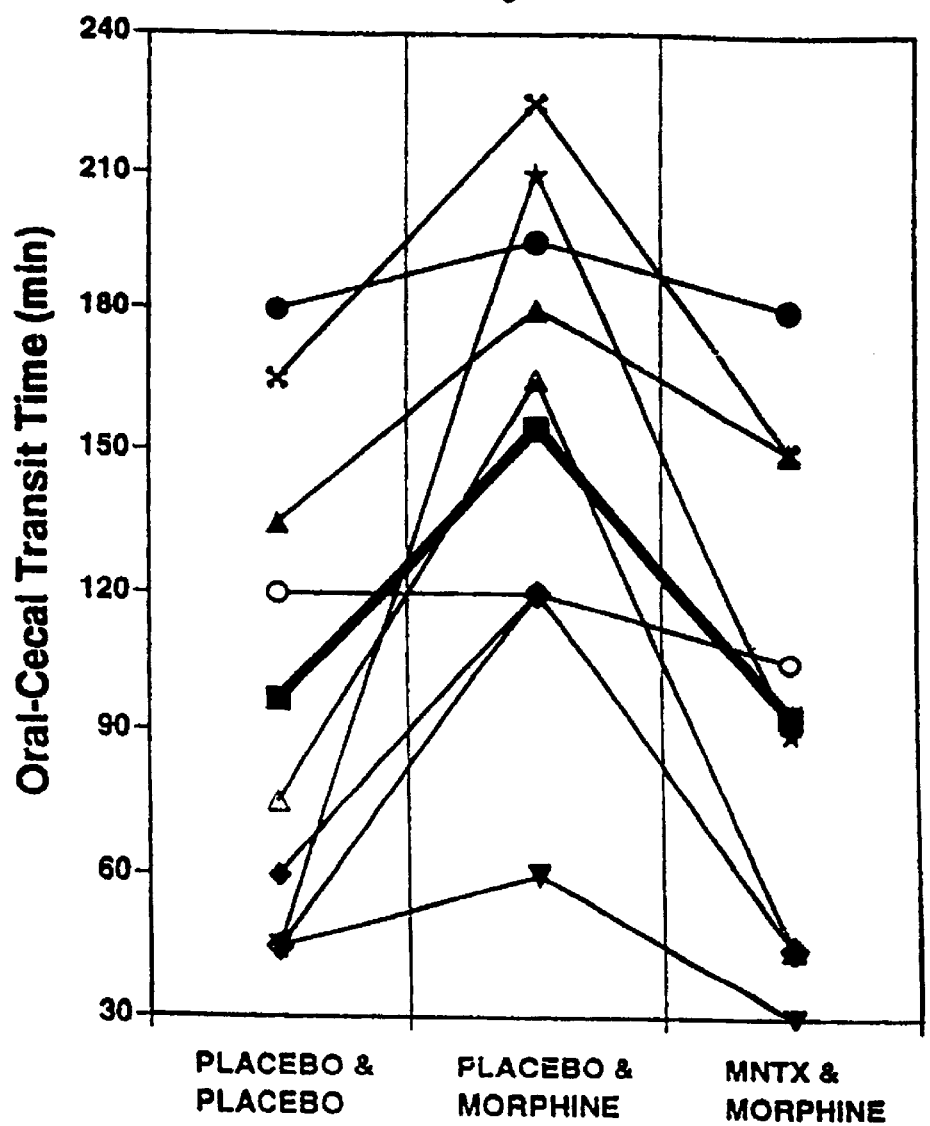

USE OF METHYLNALTREXONE AND RELATED COMPOUNDS

CROSS REFERENCE TO RELATED APPLICATIONS

This application is a continuation-in-part of Ser. No. 08/962,742, filed Nov. 3, 1997, now U.S. Pat. No. 5,972,954, the disclosure of which is herein incorporated by reference.

Partial funding of the work described herein was provided under M01 RR00055 awarded by the U.S. Public Health Service General Clinical Research Center, and the U.S. Government has certain rights in the invention.

FIELD OF THE INVENTION

The present invention is directed at the treatment of certain side effects associated with the use of opioids as analgesics. In particular the present invention is directed at treating opioid-induced inhibition of gastrointestinal motility and constipation.

BACKGROUND OF THE INVENTION

Opioids are effective analgesics. However, their use is associated with a number of undesirable side effects. One such effect is constipation. Opioid-induced changes in gastrointestinal motility are almost universal when these drugs are used to treat pain, and at times may limit their use, leaving the patient in pain. Common treatments of bulking agents and laxatives have limited efficacy and may be associated with side effects such as electrolyte imbalances.

One treatment for opioid side effects is the use of opioid antagonists which cross the blood-brain-barrier, or which are administered directly into the central nervous system. Opioid antagonists such as naltrexone and naloxone have been administered intramuscularly or orally to treat opioid induced side effects. Naltrexone and naloxone are highly lipid soluble and rapidly diffuse across biological membranes, including the blood-brain barrier. However, naltrexone, naloxone, nalmefene, and other opioid antagonists which may reverse many opioid side effects have a narrow therapeutic window before they are observed to reverse the desired analgesic effect of the opioid being used.

Many quaternary amine opioid antagonist derivatives, such as methylnaltrexone, do not reduce the analgesic effect of opioids. These quaternary amine opioid antagonist derivatives, which have a relatively higher polarity and reduced lipid solubility when compared to the tertiary forms of the drugs, were specifically developed to not traverse the blood-brain barrier or to traverse it at a greatly reduced rate. However, high levels of MNTX in the plasma can lead to undesirable side effects such as orthostatic hypotension.

It is desirable in the treatment of many conditions to have oral medications with prolonged effects. Such oral medications are particularly desirable for the treatment of opioid-induced side effects.

It is further desirable to develop a method for the prevention of opioid-induced inhibition of gut motility and constipation which does not counteract the analgesic effects of the opioid, or risk increased levels of pain. Ideally, such a treatment has few side effects either due to low drug toxicity or because administration of small amounts are effective and/or administration results in low circulating levels of the drug.

BRIEF DESCRIPTION OF DRAWINGS

FIG. 1A is a graph representing plasma concentrations of MNTX following administration of 6.4 mg/kg of uncoated MNTX.

FIG. 1B is a graph representing plasma concentrations of MNTX following administration of 6.4 mg/kg of enterically coated MNTX.

FIG. 1C is a graph representing plasma concentrations of MNTX following administration of 3.2 mg/kg of enterically coated MNTX.

FIG. 2 illustrates the reversal of morphine's effect on oral-cecal transit time following administration of 6.4 mg/kg of uncoated MNTX. The darker line represents the average of all points of a given treatment.

FIG. 3 illustrates the reversal of morphine's effect on oral-cecal transit time and its decrease below baseline following administration of 6.4 mg/kg of enterically coated MNTX. The darker line represents the average of all points of a given treatment.

FIG. 4 illustrates the reversal of morphine's effect on oral-cecal transit time following administration of 3.2 mg/kg of enterically coated MNTX. The darker line represents the average of all points of a given treatment.

SUMMARY OF THE INVENTION

The present invention is directed at methods for preventing and treating opioid-induced inhibition of gut motility and constipation.

The method for preventing opioid-induced decreased gut motility and constipation comprises administering enterically coated methylnaltrexone or other quaternary derivatives of noroxymorphone as disclosed in U.S. Pat. No. 4,176,186 to Goldberg et al. (herein incorporated by reference) to a patient prior to or simultaneously with the administration of an opioid.

The method for treating opioid-induced inhibition of gut motility and constipation comprises administering enterically coated methylnaltrexone or other quaternary derivatives of noroxymorphone to a patient after the onset of the side effect.

DETAILED DESCRIPTION

The present invention is directed to methods for preventing and treating opioid-induced constipation and changes in gut motility via the oral administration of an enteric coated quaternary derivatives of noroxymorphone (QDNM), particularly methylnaltrexone (MNTX). Administration of non-enterically coated MNTX results in rapid absorption of MNTX through the stomach and early peak and sustained high levels of MNTX in the plasma. However, an enteric coating on the QDNM, designed to prevent dissolution and subsequent absorption of the drug in the stomach, would be expected to produce delayed elevation of plasma levels of the QDNM, and to produce a lower peak plasma level. Suprisingly, however, administration of enterically coated MNTX has been found to result in substantially lower plasma levels as compared to non-enterically coated MNTX at the same dosage level, and surprisingly and unexpectedly resulted in enhanced efficacy in the reversal of opioid-induced decreases in gastrointestinal motility. In fact, it has been found that as compared to non-enterically coated MNTX, a significantly lower dose, e.g., less than half the amount of coated MNTX can be used if enterically coated to achieve the same levels of relief of opioid-induced constipation. Moreover, such reduced dosage levels of MNTX administered with an enteric coating results in exceedingly low peak and sustained plasma levels of MNTX, greatly reducing the potential adverse side effects of the MNTX. This novel improvement in the clinical indication for use of MNTX has led to an increased therapeutic index for this drug.

When used as a treatment for the opioid- and nonopioid-induced side effects of constipation and reduction of gastrointestinal motility, orally administered, particularly if enterically coated, MNTX or other quaternary derivatives of noroxymorphone provide prolonged relief of the side effects. MNTX has been demonstrated to have the ability to block the gastrointestinal effects of opioids on motility when administered intravenously or orally. The oral administration of non-enterically coated MNTX is associated with plasma levels with an early peak (20 min) and prolonged presence (half-life of about 3 hours after single dose of 6.4 mg/kg).

Furthermore, for treatment or prevention of constipation and delayed gastrointestinal emptying, whether caused by extrinsic or endogenous opioids, enteric coating surprisingly allows for equal or better efficacy despite lower plasma levels. Idiopathic constipation, i.e., that due to causes other than exogenous administration of opioids, may be mediated by opioid sensitive mechanisms. Endogenous opioid receptors have been identified in the gut, and these receptors may modulate gut motility. Thus, administration of an opioid antagonist with peripheral action, such a methylnaltrexone or other quaternary derivatives of noroxymorphone, would block the effects of endogenous opioids.

Quaternary derivatives of noroxymorphone are described in full in Goldberg et al., (supra), and in general are represented by the formula:

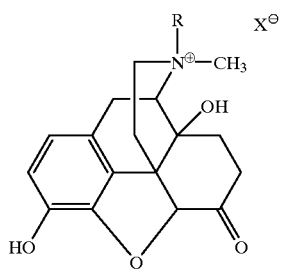

wherein R is allyl or a related radical such as chlorallyl, cyclopropyl-methyl or propargyl, and X is the anion of an acid, especially a chloride, bromide, iodide or methylsulfate anion.

The presently preferred quaternary derivative of noroxymorphone is methylnaltrexone. Methylnaltrexone is a quaternary amine derivative of naltrexone. Methylnaltrexone has been found to have only 2 to 4% of the opiate antagonistic activity of naltrexone in vivo due to its inability to pass the blood-brain-barrier and bind to the opiate receptors in the central nervous system.

Opioids are typically administered at a morphine equivalent dosage of: 0.005 to 0.15 mg/kg body weight for intrathecal administration; 0.05 to 1.0 mg/kg body weight for intravenous administration; 0.05 to 1.0 mg/kg body weight for intramuscular administration; 0.05 to 1.0 mg/kg body weight/hour for transmucosal or transdermal administration. By "morphine equivalent dosage" is meant representative doses of other opioids which equal one milligram of morphine, for example 10 mg meperidine, 1 mg methadone, and 80 µg fentanyl.

In accordance with the present invention, methylnaltrexone is administered at a dosage of: 0.1 to 40.0 mg/kg body weight for oral administration, including enteric coated methylnaltrexone.

The administration of the methylnaltrexone is preferably commenced prior to administration of the opioid to prevent opioid-induced inhibition of gastrointestinal motility or constipation. It is desirable to commence internal administration of methylnaltrexone about 20 minutes prior to administration of opioids in order to prevent these opioid-induced side effects. While the prevention of symptoms is preferred, methylnaltrexone administration may also be commenced after the administration of the opioid or after the onset of opioid induced symptoms as a treatment for those symptoms.

Methylnaltrexone is rapidly absorbed after oral administration from the stomach and bowel. Initial plasma levels of the drug are seen within 5–10 minutes of the administration of non-enteric coated compound. Addition of an enteric coating which prevents gastric absorption is associated with lower plasma levels of the methylnaltrexone. Surprisingly, the addition of an enteric coating (i.e., a coating which will prevent degradation or release in the stomach, but will release drug in the small and large bowel) enhances the efficacy of methylnaltrexone in the prevention of decreases in gut motility by intravenously administered opioids (morphine).

In a preferred embodiment for the prevention and/or treatment of constipation and inhibition of gastrointestinal motility, the QDNM or MNTX is enterically coated and administered orally. For oral administration, the QDNM or methylnaltrexone is formulated with pharmacologically acceptable binders to make a tablet or capsule with an enteric coating. An enteric coating is one which remains intact during passage through the stomach, but dissolves and releases the contents of the tablet or capsule once it reaches the small intestine. Most currently used enteric coatings are those which will not dissolve in low pH environments, but readily ionize when the pH rises to about 4 or 5, for example synthetic polymers such as polyacids having a $pK_a$ of 3 to 5.

The enteric coating may be made of any suitable composition. Suitable enteric coatings are described, for example, in U.S. Pat. No. 4,311,833 to Namikoshi, et al.; U.S. Pat. No. 4,377,568 to Chopra; U.S. Pat. No. 4,385,078 to Onda, et al.; U.S. Pat. No. 4,457,907 to Porter; U.S. Pat. No. 4,462,839 to McGinley, et al.; U.S. Pat. No. 4,518,433 to McGinley, et al.; U.S. Pat. No. 4,556,552 to Porter, et al.; U.S. Pat. No. 4,606,909 to Bechgaard et al.; U.S. Pat. No. 4,615,885 to Nakagame, et al.; U.S. Pat. No. 4,670,287 to Tsuji; U.S. Pat. No. 5,536,507 to Abramowitz, et al.; U.S. Pat. No. 5,567,423 to Ying, et al.; U.S. Pat. No. 5,591,433 to Michael, et al.; U.S. Pat. No. 5,597,564 to Ying, et al.; U.S. Pat. No. 5,609,871 to Michael, et al.; U.S. Pat. No. 5,614,222 to Kaplan; U.S. Pat. No. 5,626,875 to Rodes, et al.; and U.S. Pat. No. 5,629,001 to Michael, et al., all of which are incorporated herein by reference.

Preferred enteric coating compositions include alkyl and hydroxyalkyl celluloses and their aliphatic esters, e.g., methylcellulose, ethylcellulose, hydroxyethylcellulose, hydroxypropylcellulose, hydroxybutylcellulose, hydroxyethylethylcellulose, hydroxyprophymethylcellulose, hydroxybutylmethylcellulose, hydroxypropylcellulose phthalate, hydroxypropylmethylcellulose phthalate and hydroxypropylmethylcellulose acetate succinate; carboxyalkylcelluloses and their salts, e.g., carboxymethylethylcellulose; cellulose acetate phthalate; cellulose acetate trimellitate, polycarboxymethylene and its salts and derivatives; polyvinyl alcohol and its esters: polyvinyl acetate phthalate; polycarboxymethylene copolymer with sodium formaldehyde carboxylate; acrylic polymers and copolymers, e.g., methacrylic acid-methyl methacrylic acid copolymer and methacrylic acid-methyl acrylate copolymer; edible oils such as peanut oil, palm oil, olive oil and hydrogenated vegetable oils; polyvinylpyrrolidone; polyethylene glycol and its esters; natural products such as shellac, and zein.

Other preferred enteric coatings include polyvinylacetate esters, e.g., polyvinyl acetate phthalate; alkyleneglycolether esters of copolymers such as partial ethylene glycol monomethylether ester of ethylacrylate-maleic anhydride copolymer or diethyleneglycol monomethylether ester of methylacrylate-maleic anhydride copolymer, N-butylacrylate-maleic anhydride copolymer, isobutylacrylate-maleic anhydride copolymer or ethylacrylate-maleic anhydride copolymer; and polypeptides resistant to degradation in the gastric environment, e.g., polyarginine and polylysine. Other suitable coatings and methods to make and use such formulations are well known to those skilled in the art (see, e.g., *Remington: The Science and Practice of Pharmacy,* 19th ed. (1995) Mack Publishing Company, Easton, Pa.; herein incorporated by reference).

Mixtures of two or more of the above compounds may be used as desired. The presently preferred enteric coating comprises cellulose acetate phthalate.

The enteric coating material may be mixed with various excipients including plasticizers such as triethyl citrate, acetyl triethyl citrate, diethyl phthalate, dibutyl phthalate, dibutyl subacute, dibutyl tartrate, dibutyl maleate, dibutyl succinate and diethyl succinate and inert fillers such as chalk or pigments.

The composition and thickness of the enteric coating may be selected to dissolve immediately upon contact with the digestive juice of the intestine. Alternatively, the composition and thickness of the external coating may be selected to be a time-release coating which dissolves over a selected period of time, as is well known in the art.

The amount of enteric coating depends on the particular enteric coating composition used and is preferably sufficient to substantially prevent the absorption of MNTX in the stomach.

Hydroxyalkyl celluloses and their aliphatic esters, carboxyalkyl celluloses and their salts, polycarboxymethylene and its salts and derivatives, polyvinyl alcohol and its esters, polycarboxymethylene copolymer with sodium formaldehyde carboxylates, poly-vinylpyrrolidone, and polyethylene glycol and its esters can be applied as enteric coatings by first dissolving the compound in a minimum amount of water. Alcohol is then added to the point of incipient cloudiness. The mixture can then be applied by conventional techniques.

Application of cellulose acetate phthalate may be accomplished by simply dissolving the cellulose acetate phthalate in a minimum amount of alcohol and then applying by conventional techniques. Hydrogenated vegetable oils may be applied by first dissolving the oil in a minimal amount of a non-polymer solvent, such as methylene chloride, chloroform or carbon tetrachloride, then adding alcohol to the point of incipient cloudiness and then applying by conventional techniques.

In a particularly preferred embodiment, the MNTX is coated with Eudragit L100 or S100, a methacrylic acid copolymer enteric coating, at a 50% coating level to provide stability at gastric pH and dissolution at gut pH per a US Pharmacopeia (USP) standard for enteric coatings.

In the above description, methylnaltrexone is used as an example of a particularly effective QDNM. It is apparent that other QDNM's may be used as desired.

The following Examples are intended to illustrate aspects of the invention and are not to be construed as limitations upon it. The methylnaltrexone used in the following Examples was manufactured by Mallinckrodt Pharmaceuticals, St. Louis, Mo. The Enteric Coating was manufactured by Coating Place, Inc., Verona, Wis.

EXAMPLE 1

Effects Of Enterically Coated MNTX On Oral-Cecal Transit Time and Plasma Levels of MNTX Oral methylnaltrexone, whether enterically coated or uncoated, was shown to reverse the inhibitory effects of opioid administration on gastrointestinal motility as measured by oral-cecal transit time. As compared to non-enterically coated MNTX, however, treatment with enterically coated MNTX enhanced the efficacy of the drug at a lower dose while producing lower plasma levels of MNTX.

Subjects were divided into five treatment groups A–E. With the exception of subjects in Group A, who were given a placebo in place of morphine, all were given an intravenous dose of morphine at 0.05 mg/kg. Prior to morphine administration, subjects were given either a placebo or MNTX in various doses and formulations (see Table 1). The subjects in Group A and B were given a placebo in place of MNTX. Group C received uncoated MNTX at 6.4 mg/kg, Group D received enterically coated MNTX at 6.4 mg/kg active drug, and Group E received enterically coated MNTX at 3.2 mg/kg active drug. Table 1 shows the treatments for each group.

TABLE 1

| Group | Treatment combination | | FIG. |
|---|---|---|---|
| A | placebo | placebo | |
| B | morphine (0.05 mg/kg) | placebo | |
| C | morphine (0.05 mg/kg) | methylnaltrexone uncoated (6.4 mg/kg) | FIG. 2 |
| D | morphine (0.05 mg/kg) | methylnaltrexone enteric coated (6.4 mg/kg active drug) | FIG. 3 |
| E | morphine (0.05 mg/kg) | methylnaltrexone enteric coated (3.2 mg/kg active drug) | FIG. 4 |

Plasma levels of MNTX were measured following administration of morphine and MNTX or placebo several times over the duration of the six hour monitoring period, at the times shown in FIG. 1. Measurements of plasma and urine MNTX levels were determined by high performance liquid chromatography (HPLC) using the modified method originally reported by Kim et al. (1989) *Chromatographia* 28:359–63, herein incorporated by reference). Methylnaltrexone was separated from plasma by solid phase extraction (SPE). Plasma samples (100–500 $\mu$l) diluted in water with the internal standard (naltrexone) were passed through SPE columns. Prior to use, the columns were conditioned by methanol and washed with water. The analytes were eluted from the columns by the mixture of n-propanol and trifluoroacetic acid (25 mM) aqueous solution prepared in 2:1 proportion. The eluate was evaporated to dryness in a stream of nitrogen at 55° C. The residue was reconstituted in the mobile phase, filtered through a nylon HPLC syringe filter and subjected to HPLC analysis. A Shimadzu Corporation (Kyoto, Japan) HPLC system was used. It consisted of the LC-10AD pump, SCL-10A system controller, and SIL-10A auto injector equipped with sample cooler. Used HPLC Analytical Column made by Phenomenex (Prodigy C8, Torrance, Calif.). The electrochemical detector (ESA Coulochem, model 5100A) worked at the following settings: detector 1, +360 mV, detector 2 +600 mV, guard cell +650 mV. Data were collected with the use of EZChrom 2—2 HPLC software. The mobile phase consisted of 50 mM sodium acetate, 7.5% methanol at pH 4.2. The system was calibrated daily in the range of 5–100 ng/ml (3 point calibration). Practical limit of detection for plasma samples was approximately 2 ng/ml (100 pg/injection).

FIG. 1 shows the plasma levels of MNTX following the treatments in Groups C, D, and E. In FIG. 1A, MNTX plasma levels in Group C (given 6.4 mg/kg MNTX, uncoated) peaked at about 15 min. post-MNTX administration and remained at a roughly constant level (between about 35–50 ng/ml) for the duration of the study period (6 hours). Group D, given 6.4 mg/kg MNTX in an enterically coated formulation, exhibited a constant low plasma level of MNTX (under 10 ng/ml) for the duration of observation (see FIG. 1B). Group E, given 3.2 mg/kg MNTX in an enterically coated formulation, showed plasma levels of MNTX over the course of observation that were undetectable or at the lower limit of detection of the assay (see FIG. 1C).

Oral-cecal transit time was used as a measure of gut motility and propensity for constipation. Oral-cecal transit time was measured by the lactulose-breath hydrogen method. Group A demonstrated normal transit times as previously described in the literature (Yuan et al. (1996) *Clin. Pharmacol. Ther.* 59:469–475; Yuan et al. (1997) *Clin. Pharmacol. Ther.* 61:467–475). Group B had prolongation of their oral-cecal transit times by 50–100%, while Groups C (FIG. 2) and E (FIG. 4) had their transit times return to baseline levels. Group D showed an obvious decrease in oral-cecal transit time (FIG. 3).

As demonstrated in FIGS. 1–4, enterically coated MNTX provides the therapeutic effects on gastrointestinal motility of uncoated MNTX, but requires a lower dose of active drug and results in significantly reduced plasma levels of MNTX. Patients provided with a dose of 6.4 mg/kg of uncoated MNTX had gut motility return to baseline following morphine administration (FIG. 2) and showed plasma MNTX levels of over 40 ng MNTX/ml, while patients given the same dose in an enterically coated formulation showed oral-cecal transit times below baseline levels (FIG. 3) and plasma MNTX levels under 10 ng/ml. Enterically coated formulations of MNTX with one half the dose of active drug (3.2 mg/kg) were required to return oral-cecal transit times to I 5 normal without increasing gut motility. At this dosage, plasma levels of MNTX were negligible.

As with most drugs, it is desirable to maintain the lowest possible systemic levels of MNTX which are sufficient to provide the desired therapeutic effect. For example, elevated circulating levels of MNTX can result in orthostatic hypotension. The present discovery provides an unexpected means to avoid such undesirable drug side effects by lowering the dose administered and subsequently minimizing circulating levels of the drug. Since endogenous and externally supplied opioid-induced inhibition of gastrointestinal motility and constipation is thought to result from opioid receptors located within the gastrointestinal tract, enterically coated MNTX or other QDNMs may provide a local administration of the drug that does not require a circulating level for effective prevention or treatment of symptoms. Thus, the amount and/or frequency of drug administered can be reduced.

The preceding description and Examples are intended to be illustrative. Those skilled in the art to which the invention pertains will appreciate that alterations and changes in the described protocols may be practiced without departing from the meaning, spirit, and scope of this invention.

Therefore, the foregoing description should be read consistent with and as support to the following claims, which are to have their fullest and fair scope.

What is claimed is:

1. A method for preventing opioid induced inhibition of gastrointestinal motility comprising orally administering an enterically coated quaternary derivative of noroxymorphone to a patient prior to administration of an opioid, wherein substantially no quaternary derivative is released in the stomach.

2. The method of claim 1 wherein the quaternary derivative is methylnaltrexone.

3. The method of claim 2 wherein the methylnaltrexone is administered at a dosage a 0.1 to 40.0 mg of active drug per kg body weight.

4. The method of claim 3 wherein the methylnaltrexone is administered orally at a dosage of about 0.1 to about 10 mg/kg body weight.

5. The method of claim 2 wherein the methylnaltrexone is administered as an enterically coated tablet or capsule, or as enterically coated granules.

6. The method of claim 2 wherein the patient's plasma level of methylnaltrexone remains below 25 ng/ml.

7. The method of claim 2 wherein the enteric coating provides time release of the methylnaltrexone.

8. The method of claim 1 wherein the inhibition of gastrointestinal motility is manifested as constipation.

9. The method of claim 1 wherein the patient's peak and sustained plasma levels of the quaternary derivative are below about 50 ng/ml.

10. The method of claim 1, wherein the patient's peak blood plasma levels are lower than they would be if 10% or more of the same dose of quaternary derivative were released in the stomach and the rest was released enterically.

11. A method for treating opioid induced inhibition of gastrointestinal motility comprising orally administering an enterically coated quaternary derivative of noroxymorphone to a patient subsequent to administration of an opioid, wherein substantially no quaternary derivative is released in the stomach.

12. The method of claim 11 wherein the quaternary derivative is methlynaltrexone.

13. The method of claim 12 wherein the patient's plasma level of methylnaltrexone remains below 25 ng/ml.

14. The method of claim 12 wherein the methylnaltrexone is administered at a dosage 0.1 to 40.0 mg of active drug per kg body weight.

15. The method of claim 14 wherein the methylnaltrexone is administered orally at a dosage of about 0.1 to about 10 mg/kg body weight.

16. The method of claim 12 wherein the methylnaltrexone is administered as an enterically coated tablet or capsule, or as enterically coated granules.

17. The method of claime 12 wherein the enteric coating provides time release of the methylnaltrexone.

18. The method of claim 11 wherein the inhibition of gastrointestinal motility is manifested as constipation.

19. The method of claim 11 wherein the patient's peak and sustained plasma levels of the quaternary derivative are below about 50 ng/ml.

20. The method of claim 11, wherein the patient's blood plasma levels are lower than they would be if 10% or more of the same dose of quaternary derivative were released in the stomach and the rest was released enterically.

21. A method for treating opioid induced inhibition of gastrointestinal motility comprising orally administering an enterically coated quaternary derivative of noroxymorphone to a patient wherein the inhibition of gastrointestinal motility is induced by endogenous opioids.

22. A composition for preventing or treating opioid induced inhibition of gastrointestinal motility comprising an enterically coated quaternary derivative of noroxymorphone, which is substantially free of non-enterically coated quaternary derivative of noroxymorphone.

23. A composition as claimed in claim 22 in the form of a pill, tablet, capsule or granules.

24. A composition as claimed in claim 22 where the quaternary derivative of noroxymorphone is methylnaltrexone.

25. A method of treating or preventing opioid induced inhibition of gastrointestinal motility comprising orally administering an enterically coated quaternary derivative of noroxymorphone to a patient wherein the patient's peak plasma levels of the quaternary derivative do not exceed about 50 ng/ml.

26. The method of claim 25 wherein the patient's peak plasma levels of the quaternary derivative do not exceed about 40 ng/ml.

27. The method of claim 25 wherein the patient's peak plasma levels of the quaternary derivative do not exceed about 30 ng/ml.

28. The method of claim 25 wherein the patient's peak plasma levels of the quaternary derivative do not exceed about 20 ng/ml.

29. The method of claim 25 wherein the patient's peak plasma levels of the quaternary derivative do not exceed about 10 ng/ml.

30. The method of claim 25 wherein the patient's peak plasma levels of the quaternary derivative do not exceed about 2 ng/ml.

* * * * *